(12) United States Patent
Bi et al.

(10) Patent No.: US 9,114,170 B2
(45) Date of Patent: Aug. 25, 2015

(54) HIGHLY LOADED AMORPHOUS EFAVIRENZ COMPOSITION AND PROCESS FOR PREPARING THE SAME

(71) Applicant: ISP Investments Inc., Wilmington, DE (US)

(72) Inventors: Yunxia Bi, Garnet Valley, PA (US); Mohammed Abdul Rahman, Columbia, MA (US); James David Lester, Laurel, MA (US); Thomas Durig, Chadd Ford, PA (US); Randy Bull, Hopewell, NJ (US)

(73) Assignee: ISP INVESTMENTS INC., Wilmington, DE (US)

( * ) Notice: Subject to any disclaimer, the term of this patent is extended or adjusted under 35 U.S.C. 154(b) by 25 days.

(21) Appl. No.: 13/843,224

(22) Filed: Mar. 15, 2013

(65) Prior Publication Data
US 2014/0148449 A1    May 29, 2014

Related U.S. Application Data

(60) Provisional application No. 61/724,050, filed on Nov. 8, 2012.

(51) Int. Cl.

| | |
|---|---|
| *A61K 31/536* | (2006.01) |
| *C07D 265/14* | (2006.01) |
| *A61K 47/38* | (2006.01) |
| *A61K 47/32* | (2006.01) |
| *B29C 43/00* | (2006.01) |
| *A61K 9/14* | (2006.01) |
| *A61K 9/16* | (2006.01) |

(52) U.S. Cl.
CPC ............. *A61K 47/38* (2013.01); *A61K 9/146* (2013.01); *A61K 9/1635* (2013.01); *A61K 31/536* (2013.01); *A61K 47/32* (2013.01); *B29C 43/003* (2013.01)

(58) Field of Classification Search
CPC .......................... A61K 31/536; C07D 265/14
USPC ................... 544/88, 92; 514/228.8, 230.5
See application file for complete search history.

(56) References Cited

U.S. PATENT DOCUMENTS

2007/0026073 A1    2/2007   Doney

FOREIGN PATENT DOCUMENTS

WO    WO2012085236 A1    6/2012

OTHER PUBLICATIONS

Lamba et al, A Factorial Study on Formulation Development of Efavirenz Tablets Employing Cyclodextrin-Poloxamer 407-PVP K30 in IJPSR, 2012; vol.
International Search Report PCT/US2013/069030 mailed on May 12, 2014.

*Primary Examiner* — Golam M M Shameem
(74) *Attorney, Agent, or Firm* — William J. Davis

(57) ABSTRACT

A stable and high loading ternary solid dispersion composition comprising (a) about 50% wt. to about 90% wt. of amorphous Efavirenz; (b) about 10% wt. to about 50% wt. of polyvinyl pyrrolidone (PVP), a first polymer; (c) about 1% wt. to about 30% wt. of a water-soluble second polymer; and (d) optionally about 0.1% wt. to about 50% wt. of at least one pharmaceutically acceptable excipient. Also discloses a high loading ternary composition comprising (a) a solid dispersion composition comprising (i) about 50% wt. to about 90% wt. of amorphous Efavirenz; (ii) about 10% wt. to about 50% wt. of polyvinyl pyrrolidone, a first polymer; (b) about 1% wt. to about 30% wt. of a water-soluble second polymer blended with solid dispersion of composition of (a); and (c) optionally about 0.1% wt. to about 50% wt. of at least one pharmaceutically acceptable excipient. Additionally discloses a method for preparing solid dosage forms comprising (i) amorphous Efavirenz and (ii) polyvinyl pyrrolidone (PVP), a first polymer; (iii) a water-soluble second polymer; and (iv) optionally, at least one pharmaceutical excipients.

12 Claims, 7 Drawing Sheets

HIGHLY LOADED AMORPHOUS EFAVIRENZ COMPOSITION AND PROCESS FOR PREPARING THE SAME

CROSS REFERENCE TO RELATED APPLICATION

The present application claims benefit of U.S. Provisional Application Ser. No. 61/724,050 filed on Nov. 8, 2012, the entire contents of which are hereby incorporated by reference.

FIELD OF THE INVENTION

The present application relates to a ternary composition, and, more particularly, a highly loaded composition comprising (i) amorphous Efavirenz; (ii) polyvinyl pyrrolidone, a first polymer, and (iii) at least one water-soluble second polymer, either incorporated into the solid dispersion system, or added externally to a solid dispersion comprising (i) and (ii).

BACKGROUND OF THE INVENTION

It has been estimated that more than 60% of Active Pharmaceutical Ingredients (API) in development have poor bioavailability due to low water solubility (Manufacturing chemist, March 2010, 24-25). This percentage is likely to increase in the future with the increased use of combinatorial chemistry in drug discovery targeting lipophilic receptors. Such poorly water-soluble drugs often require high doses in order to increase their bioavailability by means of increased therapeutic plasma concentrations after oral administration. Efavirenz, (S)-6-chloro-4-(cyclopropylethynyl)-1,4-dihydro-4-(trifluoromethyl)-2H-3-1-benzoxazin-2-one, is one among such poor water-soluble drug efficient in the treatment of the human immunodeficiency virus (HIV) which is a retrovirus that causes progressive destruction of the human immune system with the resultant onset of Acquired Immune Deficiency Syndrome (AIDS). It is effectively treated through inhibition of HIV reverse transcriptase.

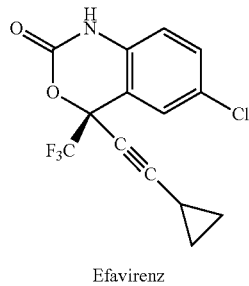 [SMILES: O=C1Nc2ccc(Cl)cc2[C@@](C#CC2CC2)(C(F)(F)F)O1]

Efavirenz

Efavirenz, a benzoxazinone found to be useful non-nucleoside based inhibitors of HIV-1 reverse transcriptase (NNRTI). Methods for the synthesis of Efavirenz are disclosed in the U.S. Pat. No. 5,519,021; U.S. Pat. No. 5,663,169; U.S. Pat. No. 5,665,720; U.S. Pat. No. 5,811,423 and U.S. Publication Nos. 20120108809; 20110196151; 20110077397; 20110071287; 20110015189, the disclosures of which are hereby incorporated by reference. Efavirenz is currently available in dosage forms containing 50 mg, 100 mg, 200 mg, and 600 mg of active. These dosage forms contain Efavirenz in microcrystalline form and one or more disintegrants such as croscarmellose sodium to aid in tablet disintegration and dissolution. As described in WO99/64405, the crystalline Efavirenz exists in several physical forms.

Efavirenz belongs to BCS Class II category and exhibits low and variable oral bioavailability due to its poor water solubility. The oral absorption of Efavirenz is limited by its dissolution rate and it requires enhancement in solubility and dissolution rate for increasing its oral bioavailability.

Amorphous solid dispersion is a proven technology that can effectively enhance the dissolution and solubility of poorly soluble compounds. A preferred amorphous solid dispersion of an active pharmaceutical ingredient (API) should demonstrate good physical stability so the amorphous API will not crystallized during the intended shelf life. In addition, amorphous solid dispersion should also be able to maintain high concentration in aqueous gastro-intestinal fluid for extended period of time, hence enhance the bioavailability of API. Due to the thermal dynamically unstable nature of amorphous form, to obtain an amorphous with both good physical stability and dissolution profile could be challenging, especially when the drug load in the solid dispersion is high.

Due to the poorly soluble nature of Efavirenz, it has been formulated as solid dispersion compositions in order to improve the dissolution behavior such poor soluble compounds (Int. J. Pharm. Sci. Rev. & Res. 2012, 17(1), pp. 97-103; J. Pharm. Sci. 2012, 101 (9), pp. 3456-3464; J. Chem. Pharm. Sci. 2012, 5 (2), pp. 35-41; Int. J. Pharm. 2010, 384 (1-2), pp. 24-31; US Publication No. 20070026073).

When formulating amorphous solid dispersions as oral dosage form, it is often desirable to maximize the drug load. This minimizes the size of the solid dosage form required to achieve the desired dose. Depending on the drug dose, a drug load of at least 50 wt %, preferably at least 60 wt %, and more preferably at least 70 wt % may become necessary. Such high drug loadings minimize the dosage form's size, making it easier for the patient to swallow it and tending to improve patient compliance.

Efavirenz has an adult daily dose of 600 mg and is dosed once per day. There is a need for immediate release dosage forms comprising high drug load amorphous solid dispersions that are physically stable and has ability to enhance the dissolution of Efavirenz in gastrointestinal tract (GIT) in order to improve the rate and amount of absorption into the body, thereby improving its therapeutic efficacy of Efavirenz.

In the present application, some of the limitations set forth above are addressed by a new ternary composition comprising (a) Amorphous Efavirenz, a poorly soluble API, (b) polyvinyl pyrrolidone, a first polymer, (c) at least one water-soluble second polymer, (d) optionally, at least one pharmaceutically acceptable excipient. Surprisingly, the ternary solid dispersion composition demonstrates superior physical stability upon storage, and/or maintained high concentration of Efavirenz in bio-relevant media more efficiently than its relevant binary amorphous solid dispersion compositions. Further, this unique ternary system is capable of providing significantly enhanced bioavailability while enhancing patient compliance by reducing the size of the solid dosage due to its high drug load.

SUMMARY OF THE INVENTION

The present application provides a stable and high loading ternary composition comprising (a) about 50% wt. to about 90% wt. of amorphous Efavirenz; (b) about 10% wt. to about 50% wt. of polyvinyl pyrrolidone, a first polymer; (c) about 1% wt. to about 30% wt. of water-soluble second polymer; and (d) optionally about 0.1% wt. to about 50% wt. of at least one pharmaceutically acceptable excipient.

According to one important aspect of the present application, the ratio of (a) Efavirenz (b) to first polymer (c) to water-soluble second polymer is about 1.0:0.5-1.0:0.05-0.5.

Another important aspect of the present application is to provide various methods to prepare solid dispersion composition comprising (a) about 50% wt. to about 90% wt. of amorphous Efavirenz; (b) about 10% wt. to about 50% wt. of PVP, a first polymer; (c) about 1% wt. to about 30% wt. of water-soluble second polymer; and (d) optionally about 0.1% wt. to about 50% wt. of at least one pharmaceutically acceptable excipient.

Yet another aspect of the present application provides various methods for preparing said solid dispersion composition comprising spray-drying, hot-melt extrusion, solvent-evaporation, melt-granulation, melt-congealing, spray-congealing, blending, co-milling, spray coating, fluid bed granulation, layering and/or coating.

Another important aspect of the present application provides a method for preparing a dosage form comprising the steps of (a) preparing spray-dried solid dispersion composition of Efavirenz and polyvinyl pyrrolidone, a first polymer; and (b) blending the resulting solid dispersion powder of step (a) with a desired second polymer; (c) optionally adding at least one pharmaceutically acceptable excipients and (d) making the final dosage form from the resultant mixture of step (c).

One important aspect of the present application provides a method for preparing a tablet dosage form comprising the steps of (a) preparing spray-dried solid dispersion composition of Efavirenz and polyvinyl pyrrolidone, a first polymer; and (b) compressing the resulting solid dispersion powder of step (a) into a solid oral dosage form, preferably a tablet; and (c) coating the resultant solid oral dosage form of step (b) with a desired water-soluble second polymer.

According to additional aspect of the present application, the desired solid dispersion composition further comprises a pharmaceutically acceptable excipients selected from the group consisting of plasticizers, disintegrants, surfactants, lubricants, glidants, carriers, anti-adherents, fillers, wetting agents, pH modifiers, binders, solubility modifiers, recrystallization inhibitors, coating agent and/or diluents.

BRIEF DESCRIPTION OF THE DRAWINGS

Further embodiments of the present invention can be understood with the appended figures.

DETAILED DESCRIPTION OF THE INVENTION

Figure 1:
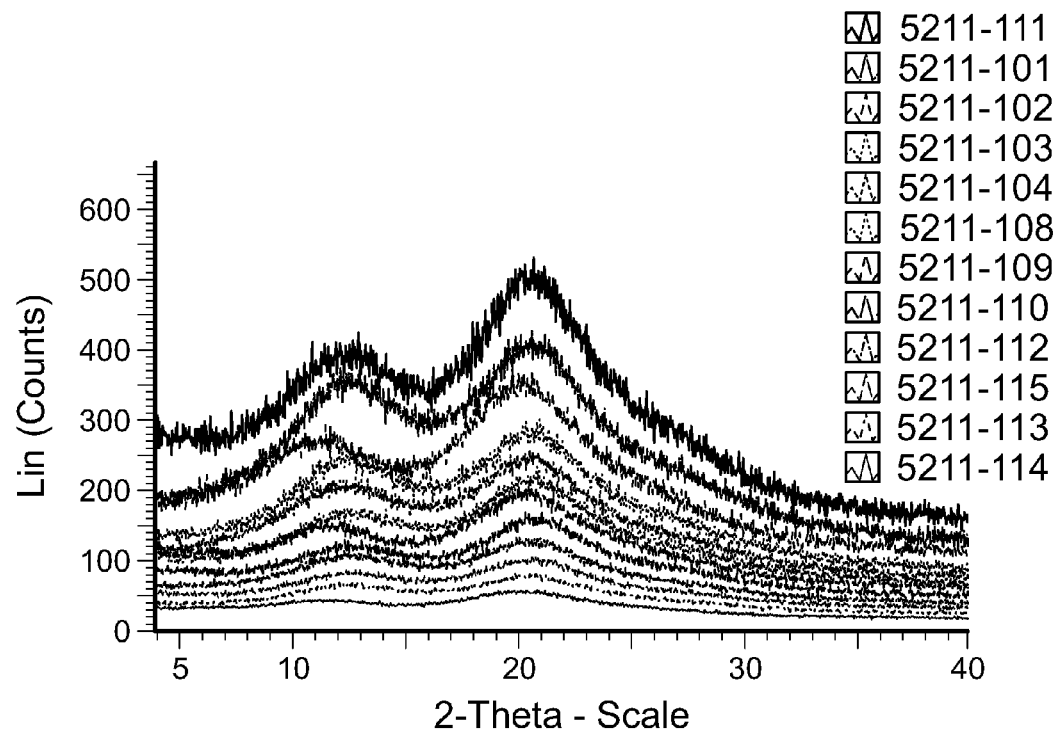
FIG. 1 is an illustration of XRPD patterns of binary and co-processed ternary spray-dried solid dispersions (5211-101 to 104; and 5211-108 to 115).

While this specification concludes with claims particularly pointing out and distinctly claiming that which is regarded as the invention, it is anticipated that the invention can be more readily understood through reading the following detailed description of the invention and study of the included examples.

The singular forms "a," "an," and "the" include plural forms unless the context clearly dictates otherwise specified or clearly implied to the contrary by the context in which the reference is made. The term "Comprising" and "Comprises of" includes the more restrictive claims such as "Consisting essentially of" and "Consisting of".

The term "about" can indicate a difference of 10 percent of the value specified. Numerical ranges as used herein are meant to include every number and subset of numbers enclosed within that range, whether particularly disclosed or not. Further, these numerical ranges should be construed as providing support for a claim directed to any number or subset of numbers in that range.

All percentages, parts, proportions and ratios as used herein, are by weight of the total composition, unless otherwise specified. All such weights as they pertain to listed ingredients are based on the active level and, therefore; do not include solvents or by-products that may be included in commercially available materials, unless otherwise specified.

All references to singular characteristics or limitations of the present invention shall include the corresponding plural characteristic or limitation, and vice-versa, unless otherwise specified or clearly implied to the contrary by the context in which the reference is made.

As used herein, the words "preferred" or "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

References herein to "one embodiment" or "one aspect" or "one version" or "one objective" of the invention include one or more such embodiment, aspect, version or objective, unless the context clearly dictates otherwise.

All publications, articles, papers, patents, patent publications, and other references cited herein are hereby incorporated herein in their entirety for all purposes to the extent consistent with the disclosure herein.

The term "polymer" refers to a compound comprising repeating structural units (monomers) connected by covalent chemical bonds. Polymers may be further derivatized, crosslinked, grafted or end-capped. Non-limiting examples of polymers include copolymers, terpolymers, quaternary polymers, and homologues. The term "copolymer" refers to a polymer consisting essentially of two or more different types of repeating structural units (monomers).

The present application describes a stable and high loading ternary solid dispersion composition comprising (a) about 50% wt. to about 90% wt. of amorphous Efavirenz; (b) about 10% wt. to about 50% wt. of polyvinyl pyrrolidone (PVP), a first polymer; (c) about 1% wt. to about 30% wt. of a water-soluble second polymer; and (d) optionally about 0.1% wt. to about 50% wt. of at least one pharmaceutically acceptable excipient.

This application also discloses a high loading ternary composition comprising (a) a solid dispersion composition comprising (i) about 50% wt. to about 90% wt. of amorphous Efavirenz; (ii) about 10% wt. to about 50% wt. of polyvinyl pyrrolidone, a first polymer; (b) about 1% wt. to about 30% wt. of a water-soluble second polymer blended with solid dispersion of composition of (a); and (c) optionally about 0.1% wt. to about 50% wt. of at least one pharmaceutically acceptable excipient.

The term "Pharmaceutically acceptable excipient" is an additive included to a solid formulations in the form such as powders, granules, capsules, pellets and tablets to increase the bulk of the desired formulation comprising present solid dispersion. Wherein, the excipients may be added during or after the preparation of hot-melt or spray-dried form of solid dispersion composition.

"Efavirenz" refers to a pharmacologically active ingredient (S)-6-chloro-4-(cyclopropylethynyl)-1,4-dihydro-4-(trifluoromethyl)-2H-3-1-benzoxazin-2-one. The process for the preparing this compound is described in prior arts which are known to a person skilled in the art.

According to one important embodiment of the present application, it employs Efavirenz, a poor water soluble BCS Class II drug for the preparation of stable and high loading amorphous ternary composition. The amorphous Efavirenz solid dispersion of present application is prepared according to the methods that are known in the prior art. A particular method for preparing said amorphous Efavirenz is disclosed in US Publication No. 20060235008, US Publication No. 20070026073 and US Publication No. 20120115857.

The amorphous form of Efavirenz of the present application can be a pharmaceutically acceptable enantiomer, a pharmaceutically acceptable derivative, pharmaceutically acceptable ester, pharmaceutically acceptable amide or a pharmaceutically acceptable prodrug thereof.

The Efavirenz employed in the present application is from about 50 wt. % to about 90 wt. % of amorphous Efavirenz. The other preferred ranges of Efavirenz for preparing a stable and high loading ternary solid dispersion composition of present application includes but not limited to 50 wt. % to 55 wt. %; 55 wt. % to 60 wt. %; 60 wt. % to 65 wt. %; 65 wt. % to 70 wt. %; 70 wt. % to 75 wt. %; 75 wt. % to 80 wt. %; 80 wt. % to 85 wt. %; or 85 wt. % to 90 wt. %. The most preferred range of Efavirenz for the present application is 60 wt. % to 80 wt. %.

According to one important embodiment of the present application, the stable and high loading amorphous Efavirenz ternary composition comprises polyvinylpyrrolidone (PVP), a water-soluble homopolymers of N-vinyl-2-pyrrolidone. It is readily soluble in water, physiologically compatible, non-toxic, chemically inert, temperature-resistant, pH-stable, nonionic, and colorless. These significant properties allowed its use in various applications in medicine, pharmaceutical technology, cosmetics, and in the array of technical industry.

PVP polymers are synthesized by, for example, Reppe's process, comprising: (1) obtaining 1,4-butanediol from acetylene and formaldehyde by the Reppe butadiene synthesis; (2) dehydrogenating the 1,4-butanediol over copper at 200° C. to result in γ-butyrolactone; and (3) reacting resultant γ-butyrolactone with ammonia to yield pyrrolidone. Subsequent treatment with acetylene gives the vinyl pyrrolidone monomer. Polymerization is carried out by heating in the presence of water and ammonia (*Merck Index*, 10$^{th}$ Edition, page 1106 (Merck & Co., Rahway, N.J., 1983).

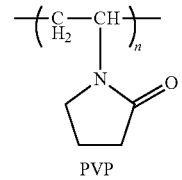

PVP

The pyrrolidone ring imparts water solubility and surfactant-like properties for high adhesion and interfacial activity. This combination of properties gives PVP polymers excellent binding performance. As physical and mechanical properties vary with a polymer's molecular weight, PVP polymers are manufactured in a variety of molecular weight grades to best meet the requirements of each application. In general, as the molecular weight of the polymer increases, the solution viscosity, glass transition temperature and adhesive properties increase. As the molecular weight decreases, the rate of polymer dissolution, oral absorption and excretion increase. PVP polymers are completely soluble in water at room temperature. The maximum concentration of polymer soluble in water is limited only by the viscosity at a given concentration. The viscosity of an aqueous solution depends on the molecular weight of the polymer. In addition to water, PVP polymers are soluble in a wide variety of organic solvents at room temperature. The viscosity of the solution is related to the viscosity of the solvent selected, the molecular weight of the polymer and concentration.

The preferred range of PVP employed in the present invention is from about 10% wt. to about 50% wt. The other preferred ranges of PVP, a water-soluble polymer for preparing a stable and high loading ternary solid dispersion composition of present application includes but not limited to 10 wt. % to 20 wt. %; 20 wt. % to 30 wt. %; 30 wt. % to 40 wt. %; 40 wt. % to 50 wt. %. The most preferred range of crospovidone is the range of from about 20% wt. to about 30% wt.

The non-limiting commercially available PVP products are sold by a number of manufacturers/suppliers. The molecular weights for these grades may vary from about 2,500 to about 3000,000 Daltons. PVP is commercially available as Plasdone® (Ashland Specialty Ingredients, Wilmington, Del.), Kollidon® (BASF Corp. Ludwigshafen, Del.), Peristone® (General Aniline). PVP is commercially available in different viscosity or molecular weight grades identified by their K-Values. The different grades of PVP are K-12, K-17, K-25, K-30, K-29/32, K-60, K-90, and K-120. The K value of PVP is calculated from the viscosity of the PVP in aqueous solution, relative to that of water.

According to another embodiment, the water-soluble second polymer is selected from the group consisting of cellulose esters, cellulose ethers, polyacrylates, polymethacrylates, acrylates co-polymers, homo and co-polymers of acrylic acids, homo and co-polymers of methacrylic acids, co-polyacrylamides, polyvinyl alcohols, polyvinylpyrrolidone, polyvinylpyrrolidone/vinyl acetate copolymer, carboxyvinyl polymers, oligosaccharides, and/or polysaccharides.

Examples of typical water-soluble second polymer species include, but are not limited to the following species hydroxypropyl methyl cellulose succinate, cellulose acetate succinate, methyl cellulose acetate succinate, ethyl cellulose acetate succinate, hydroxypropyl cellulose acetate succinate, hydroxypropyl methyl cellulose acetate succinate (HPMCAS), hydroxypropyl cellulose acetate phthalate succinate, cellulose propionate succinate, hydroxypropyl cellulose butyrate succinate, hydroxypropyl methyl cellulose phthalate (HPMCP), cellulose acetate phthalate, methyl cellulose acetate phthalate, ethyl cellulose acetate phthalate, hydroxypropyl cellulose acetate phthalate, hydroxypropyl methyl cellulose acetate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, ethyl picolinic acid cellulose acetate, carboxy methyl cellulose, carboxy ethyl cellulose, ethyl carboxy methyl cellulose, hydroxypropyl methyl cellulose acetate, hydroxypropyl methyl cellulose (HPMC), hydroxypropyl cellulose, methyl cellulose, hydroxyethyl methyl cellulose, hydroxyethyl cellulose acetate, and hydroxyethyl ethyl cellulose, copolymers of methacrylates, copolymers of acrylates, poly(methacylic acid-co-methyl methacrylate), alone or in combination.

The water-soluble second polymer is employed in an amount sufficient to form a desired composition. For certain embodiments, the water-soluble polymer will be present in an amount by weight percent of about 1.0% wt. to about 30% wt.

The other preferred ranges of a water-soluble second polymer for preparing a stable and high loading ternary solid dispersion composition of present application includes but not limited to 1 wt. % to 5 wt. %; 5 wt. % to 10 wt. %; 10 wt. % to 15 wt. %; 15 wt. % to 20 wt. %; 20 wt. % to 25 wt. %; or 25 wt. % to 30 wt. %; The most preferred range of second polymer is in the range of from about 5% wt. to about 20% wt.

It is contemplated to use other possible water soluble second polymer to prepare the ternary composition would include but not limited to acid, ester, amide or salts of olefinic polymers, lactam/pyrrolidone based polymers, pyrrolidone co-polymers, vinylpyrrolidone co-polymers, alpha-olefin maleic acid/ester co-polymers, alpha-olefin polymers, carbohydrate based polymers, polyvinyl alcohols, oligosaccharides, polysaccharides, natural polymers, gums, homopolymers of N-vinyllactam, copolymers of N-vinyllactam, homopolymers of vinylpyrrolidone, copolymers of vinylpyrrolidone, polyalkylene oxides, vinyl acetate polymers, copolymers or vinylacetate, carboxyvinyl polymers, Lactam/Pyrrolidone based polymers, Polyvinyl pyrrolidone/polyvinyl caprolactam, Pyrrolidone co-polymers, Vinyl acetate-Vinylpyrrolidone (VA/VP) co-polymers, Alkylated graft Vinylpyrrolidone co-polymers, Dimethylaminoethylmethacrylate, Vinylpyrrolidone co-polymers, Acrylic acid/Acrylic ester/Acrylic salt—Vinylpyrrolidone co-polymers, Vinylpyrrolidone/Vinyl caprolactam co-polymers, Alpha olefin maleic acid/ester co-polymers, Styrene maleic acid co-polymers, Alkyl vinyl ether-maleic acid/ester/salts co-polymers, Alpha olefin Polymers: Polyacrylates/polyvinyl derivatives, Poly alkylacrylate/alkylacrylic esters/amides/salts, Polyvinyl alcohol/acetates, Natural polymers, Cellulosic derivatives, Modified Starch, alginates, oils, beeswax, carnauba wax, microcrystalline wax, fatty alcohols, cetostearyl alcohol, stearyl alcohol, cetyl alcohol, myristyl alcohol, fatty acid esters, glyceryl monostearate, glycerol distearate, glycerol monooleate, acetylated monoglycerides, tristearin, tripalmitin, cetyl esters wax, glyceryl palmitostearate, glyceryl behenate, celluloses, ethylcellulose, low substituted hydroxypropyl cellulose (L-HPC), cellulose acylate, cellulose diacylate, cellulose triacylate, cellulose acetate, cellulose diacetate, cellulose triacetate, mono cellulose alkanylates, di-cellulose alkanylates tri-cellulose alkanylates, mono cellulose arylates, di-cellulose arylates, tri-cellulose arylates, mono cellulose alkenylates, di-cellulose alkenylates, tri-cellulose alkenylates, ethyl acrylate-methyl methacrylate-trimethylammonioethyl methacrylate chloride copolymer, methacrylic acid-ethyl acrylate copolymer, methacrylic acid-methyl methacrylate copolymer, carboxymethylcellulose sodium (carmellose sodium), croscarmellose sodium, acacia, tragacanth, propylene glycol alginate, agar powder, gelatin, starch, partly pregelatinized starch, oil, sodium starch glycolate, phospholipid (lecithin), glucomannans, polymethacrylic acid based polymers, zein, aliphatic polyesters, or mixtures of any two or more in various ratios and proportions as required without limitation.

The ratio of Efavirenz (a) to PVP, a first polymer (b) to second water-soluble polymer (c) is from about 1.0:0.5-1.0:0.05-0.5. The preferred ratio is from about 1.0:0.4-0.8:0.1-0.3.

Suitable surfactant or surfactant system for preparing a stable high loading ternary solid dispersion composition of the present application can be selected from anionic, nonionic, amphoteric, cationic and mixtures thereof. The contemplated and non-limiting list of surfactants for the present application is as follows:

(A) Anionic Surfactants: Anionic surfactants are particularly useful in accordance with certain embodiments of the present application. Surfactants of the anionic type that may be useful include:

(1) Sulfonates and Sulfates: Suitable anionic surfactants include sulfonates and sulfates such as alkyl sulfates, alkyether sulfates, alkyl sulfonates, alkylether sulfonates, alkylbenzene sulfonates, alkylbenzene ether sulfates, alkylsulfoacetates, secondary alkane sulfonates, secondary alkylsulfates, alkyl sulfosuccinates and the like. Further, examples of anionic surfactants include water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like.

(2) Phosphates and Phosponates: Suitable anionic surfactants also include phosphates such as alkyl phosphates, alkylether phosphates, aralkylphosphates, and aralkylether phosphates. Examples include a mixture of mono-, di- and tri-(alkyltetraglycolether)-o-phosphoric acid esters generally referred to as trilaureth-4-phosphate commercially available under the trade designation HOSTAPHAT 340KL from Clariant Corp., as well as PPG-5 ceteth 10 phosphate available under the trade designation CRODAPHOS SG from Croda Inc., Parsipanny, N.J.

(3) Amine Oxides: Suitable anionic surfactants also include amine oxides. Examples of amine oxide surfactants include lauryldimethylamine oxide, laurylamidopropyldimethylamine oxide, and/or cetyl amine oxide.

(B) Amphoteric Surfactants: Surfactants of the amphoteric type include surfactants having tertiary amine groups which may be protonated as well as quaternary amine containing zwitterionic surfactants. Those that may be useful include:

(1) Ammonium Carboxylate Amphoterics: Examples of such amphoteric surfactants include, but are not limited to: certain betaines such as cocobetaine and cocamidopropyl betaine; monoacetates such as sodium lauroamphoacetate; diacetates such as disodium lauroamphoacetate; amino- and alkylamino-propionates such as lauraminopropionic acid.

(2) Ammonium Sulfonate Amphoterics: These classes of amphoteric surfactants are often referred to as "sultaines" or "sulfobetaines" for example, cocamidopropylhydroxysultaine.

(C) Nonionic Surfactants: Surfactants of the nonionic type that may be particularly useful include:

(1) Polyethylene oxide extended sorbitan monoalkylates (i.e. Polysorbates); (2) Polyalkoxylated alkanols; (3) Polyalkoxylated alkylphenols include polyethoxylated octyl or nonyl phenols having HLB values of at least about 14, which are commercially available under the trade designations ICONOL and TRITON; (4) Polaxamers. Surfactants based on block copolymers of ethylene oxide (EO) and propylene oxide (PO) may also be effective. Both EO-PO-EO blocks and PO-EO-PO blocks are expected to work well as long as the HLB is at least about 14, and preferably at least about 16. Such surfactants are commercially available under the trade designations PLURONIC and TETRONIC from BASF; (5) Polyalkoxylated esters—Polyalkoxylated glycols such as ethylene glycol, propylene glycol, glycerol, and the like may be partially or completely esterified, i.e. one or more alcohols may be esterified, with a ($C_8$ to $C_{22}$) alkyl carboxylic acid. Such polyethoxylated esters having an HLB of at least about 14, and preferably at least about 16, may be suitable for use in compositions of the present invention; (6) Alkyl Polyglucosides—This includes glucopon 425, which has a ($C_8$ to $C_{16}$) alkyl chain length with an average chain length of 10.3 carbons and 14 glucose units.

(D) Cationic Surfactants: Surfactants of the cationic type that may be useful include but are not limited to, primary amines, secondary amines, tertiary amines, quaternary amines, alkanolamines, mono-alkyl alkanolamines, di-alkyl alkanolamines, tri-alkyl alkanolamines, alkyl mono alkanolamines, alkyl di-alkanolamines, alkylamines, mono-alkyl amines, di-alkyl amines, tri-alkylamines, alkoxylated amines, alkyl and aryl amine alkoxylates, methoxylated alkylamines, ethoxylated alkylamines, alkoxylated alkanolamines, alkyl alkanolamines, alkoxylated ethylene diamine derivatives, alkyl/aryl/arylalkyl amine oxides. Preferred cationic surfactants of the present invention include, but are not limited to, (a) alkyl alkanolamines; and (b) alkyl tertiary amines. Additional information on useful cationic surfactants for the purpose of present invention is set forth in McCutcheon's Detergents and Emulsifiers, North American Ed., 1982 and Kirk-Othmer, Encyclopedia of Chemical Technology, $3^{rd}$ Ed., Vol. 22, pp. 346-387, the contents of which are incorporated herein by reference.

Particularly, the preferred surfactants include dodecanesulfonic acid, sodium dodecyl sulfate, sodium lauryl sulfate (SLS), (poly)-oxyethylene sorbitan long-chain fatty acid esters, Vitamin E-TPGS, bile salts, sodium deoxycholate, sodium glycocholate and/or polyoxyethylene polyoxypropylene glycols. If desired, combinations of various surfactants can be used for the preparation of high loading ternary composition of amorphous Efavirenz.

The suitable plasticizers employed in the present application include by way of example and without limitation, acetyl triethyl citrate, acetyl tributyl citrate, triethyl citrate, acetylated monoglycerides, glycerol, polyethylene glycol, triacetin, propylene glycol, dibutyl phthalate, diethyl phthalate, isopropyl phthalate, dimethyl phthalate, dibutyl sebacate, dimethyl sebacate, castor oil, glycerol monostearate, fractionated coconut oil, low molecular weight polymers, oligomers, copolymers, oils, small organic molecules, low molecular weight polyols having aliphatic hydroxyls, ester-type plasticizers, glycol esters, poly(propylene glycol), multi-block polymers, single-block polymers, low molecular weight poly(ethylene glycol), citrate ester-type plasticizers, triacetin, propylene glycol, glycerin, ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate, polyethylene glycols such as PEG 200, PEG 300, PEG 400 and PEG 600, and/or allyl glycolate. The most preferred plasticizer for the present application is selected from the group consisting of Triethyl Citrate, Glycerol Monostearate, Dibutyl Sebacate, Diethyl Phthalate, Polyethylene Glycol, Triacetin, Vitamin E-TPGS, Tween 80, Sodium Lauryl Sulfate, Sodium Docusate, Poloxamer F-68, Poloxamer F-127, Hydroxypropyl cellulose, polyvinyl caprolactam-polyvinyl acetate-polyethylene glycol graft copolymer, alone or in combination.

According to one embodiment of the present application, at least one disintegrating agent can be added to the ternary solid dispersion composition to facilitate the breakup or disintegration of a formulation when contacted with gastrointestinal (GIT) fluid. The suitable disintegrant can be selected from the group including, but not limited to, calcium carbonate, methylcellulose, cross-linked carboxymethylcellulose, cross-linked sodium carboxymethylcellulose, calcium carboxymethyl cellulose, low-substituted hydroxypropyl cellulose, carmellose, carmellose sodium, carmellose calcium, croscarmellose sodium, agar, guar, locust bean, karaya, pectin, tragacanth, bentonite, cation-exchange resin, polyvinylpyrrolidone, crosslinked polyvinyl pyrrolidone, alginic acid, alginates, sodium alginate, microcrystalline cellulose, polacrillin potassium, starch, pregelatinized starch, carboxymethyl starch, corn starch, potato starch, sodium starch glycolate, citrus pulp, sodium lauryl sulfate, sodium lauryl sulfate alone or in combination.

Lubricants and Glidants can be employed in the present application to prevent, reduce or inhibit adhesion or friction of ingredients of the composition. They facilitate the compression and ejection of compressed compositions from a desired die. They are compatible with the ingredients of the pharmaceutical composition, and they do not significantly reduce the solubility, hardness, chemical stability, physical stability, or the biological activity of the pharmaceutical composition. The pharmaceutically acceptable lubricants and glidants for the present application are selected from the group including but not limited to stearic acid, metallic stearates, zinc stearate, magnesium stearate, magnesium trisilicate, calcium hydroxide, tribasic calcium phosphate, magnesium carbonate, magnesium oxide, calcium stearate, glyceryl monostearate, waxes, glycerides, glyceryl behenate, glyceryl palmitostearate, silicone oil, hydrogenated vegetable oil, hydrogenated castor oil, light mineral oil, mineral oil, polyethylene glycol, methoxypolyethylene glycol, sodium acetate, sodium oleate, sodium chloride, leucine, sodium benzoate, alkyl sulfates, sodium lauryl sulfate, sodium stearyl fumarate, talc, colloidal silica, corn starch, powdered cellulose, and/or boric acid. The preferred range of lubricants/glidants is from about 0.5% to 10% of the composition.

According to one embodiment of the present application, suitable binders can be selected from the group including, but not limited to, starches, modified starches, pregelatinized starch, partially pregelatinized starch, agar, gelatin, dextrin, alginic acid, sodium alginate, agar, calcium carrageenan, tragacanth gum, xanthan gum, gum acacia, sugars, lactose, liquid glucose, guar gum, hyaluronic acid, pectin, wax binders, sodium chondroitin sulfate, polyvinylpyrrolidone, povidone, polyvinyl alcohol, carboxyvinyl polymer, polyacrylic acid-series polymer, polylactic acid, polyethylene glycol, cellulose ethers, methyl cellulose, ethyl cellulose, carboxymethyl cellulose, carboxymethyl cellulose sodium, hydroxyethyl cellulose, hydroxypropyl cellulose, hydroxypropyl methyl cellulose, microcrystalline cellulose, and/or polyethylene oxides.

The desired pH of the composition can be achieved by employing any suitable pH modifying agents. The non-limiting pH modifiers include weak carboxylic acids, citric acid, acetic add, lactic acid, tartaric acid, aspartic acid, succinic acid, phosphoric acid, salicylic acid, sulfamic acid, benzoic acid or their salts, phosphates, pyrophosphate and its salts, metaphosphate and its salts, carbonic acid and its salts, hydroxylammonium, adidic acid and its salts, maleic acid and its salts, ascorbic acid and its salts, sodium acetate, potassium acetate, calcium oxide, magnesium oxide, trisodium phosphate, sodium hydroxide, ammonium hydroxide, potassium hydroxide, calcium hydroxide, aluminum hydroxide, amines, triethanol amine, diethanol amine, monoethanol amine.

Diluents or Filling agents increase the bulk of the composition to ease compression or produce sufficient bulk for homogenous blend for the composition. The appropriate diluents for the present application are selected from the following non-limiting examples including lactose, anhydrous lactose, spray-dried lactose, mannitol, sorbitol, compressible sugar, starch, sucrose, dextrose, trehalose, maltose, xylitol, lactitol, amylase, calcium sulfate, calcium sulfate dehydrate, calcium lactate trihydrate, monobasic calcium sulfate monohydrate, calcium carbonate, tribasic calcium phosphate, dibasic calcium phosphate, maltodextrin, starch, modified starch, starch hydrolyzates, pregelatinized starch, microcrystalline starches, microcrystalline cellulose, powdered cellulose, cellulose and cellulose derivatives, hydroxypropylmethylcellulose, hydroxypropylmethylcellulose acetate stearate, glycine, kaolin, sodium chloride, inositol, bentonite.

One important embodiment of the application is a process for preparing a stable high Efavirenz loading solid dispersion comprising the steps of: (i) preparing a homogeneous aqueous and/or organic solution of (a) Efavirenz, (b) polyvinyl pyrrolidone, a first polymer, and (c) a water-soluble second polymer; and (ii) spray-drying the resultant homogenous solution of step (i) to yield dry powder form of solid dispersion composition. The organic solution of step (i) is prepared from alcohols, ketones, alkyl acetates, chlorinated solvents, heterocyclic solvents, tetrahydrofuran and combination thereof.

The appropriate organic solvents for the preparation of high loading solid dispersions of present application should have significantly low toxicity and readily be removed from the solid dispersion to a level that is acceptable as per the International Committee on Harmonization (ICH) guidelines. The preferred solvents comprises alcohols, methanol, ethanol, n-propanol, iso-propanol, butanol, ketones, acetone, methyl ethyl ketone, methyl iso-butyl ketone, esters, ethyl acetate, butyl acetate, propylacetate, nitriles, acetonitrile, hydrocarbons, hexane, cyclohexane, toluene, halogenated hydrocarbons, methylene chloride, 1,1,1-trichloroethane, chloroform, ethers, cylic ethers, tetrahydrofuran, dioxane, ethyl ether, propyl ether, amides, dimethyl acetamide, dimethylsulfoxide, dimethylformamide, cellosolve, ethyl cellosolve, cellosolve acetate, methylcarbitol, N-methylpyrrolidone, organic acids, acetic acid alone or in combination. If required, pharmaceutically acceptable grade of water can be mixed with the desired organic solvent without disturbing the solubility of the API. The preferred solvents or mixture of solvents employed in the present application comprises Acetone:Water (9:1), Benzene:Methanol (1:1), Glycerin:Water (3:7), t-Butanol:Water (9:1), Toluene:Ethanol (3:2), THF:Methanol (2:1), Acetone:Methanol (2:1), Dichloromethane:Methanol (2:1), Chloroform, Cyclohexanone, Dimethyl formamide, Dimethyl sulfoxide, Dioxane, Ethylene chlorohydrin, Formic acid (88%), Tetrahydrofuran (THF).

The organic solvent can be eliminated by spray-drying through the techniques that are known in the prior art for an artisan. Moreover, the spray-drying processes and spray-drying equipment are described in detail in Perry's Chemical Engineers' Handbook, pages 20-54 to 20-57 ($6^{th}$ Edn. 1984). More details on spray-drying processes and equipment are reviewed by Marshall, "Atomization and Spray-Drying," 50 Chem. Eng. Prog. Monogr. Series 2 (1954), and Masters, Spray Drying Handbook ($4^{th}$ Edn. 1985). The driving force for solvent elimination or evaporation is usually provided by keeping the partial pressure of solvent in the spray-drying equipment substantially below the vapor pressure of the solvent at the temperature of the drying droplets.

Another embodiment of the present application relates to a method for preparing an amorphous Efavirenz ternary composition comprising the steps of: (i) preparing a homogenous aqueous and/or organic solution of (a) Efavirenz, and (b) polyvinyl pyrrolidone, a first polymer; (ii) spray-drying the resultant homogenous solution of step (i) to yield a dry powder form of desired solid dispersion; and (iii) blending the resultant solid dispersion of step (ii) with a water-soluble second polymer to yield an amorphous Efavirenz ternary composition. The organic solution of step (i) is prepared from alcohols, ketones, alkyl acetates, chlorinated solvents, heterocyclic solvents, tetrahydrofuran and combination thereof.

Yet another embodiment of the present application relates to a method for preparing an amorphous Efavirenz ternary composition comprising the steps of: (i) preparing a homogenous aqueous and/or organic solution of (a) Efavirenz, and (b) polyvinyl pyrrolidone, a first polymer; (ii) spray-drying the resultant homogenous solution of step (i) to yield a dry powder form of desired solid dispersion; and (iii) blending the resultant solid dispersion of step (ii) with a water-soluble second polymer and at least another pharmaceutical excipient to yield targeted composition; and wherein said organic solution is prepared from alcohols, ketones, alkyl acetates, chlorinated solvents, heterocyclic solvents, tetrahydrofuran and combination thereof.

Still another embodiment of the present application relates to a method for preparing a tablet dosage form comprising the steps of: (i) preparing a homogenous aqueous and/or organic solution of (a) Efavirenz, and (b) polyvinyl pyrrolidone, a first polymer; (ii) spray-drying the resultant homogenous solution of step (i) to yield a dry powder form of desired solid dispersion; (iii) optionally, adding at least another desired pharmaceutical excipients; (iv) compressing the resulting solid dispersion powder of step (iii) into a tablet dosage form; and (v) coating the resultant tablet of step (iii) with a water-soluble second polymer; and wherein said organic solution is prepared from alcohols, ketones, alkyl acetates, chlorinated solvents, heterocyclic solvents, tetrahydrofuran and combination thereof.

Another embodiment of the present application relates to a method for preparing an amorphous Efavirenz ternary composition comprising the steps of: (i) preparing a homogenous blend of (a) Efavirenz, (b) polyvinyl pyrrolidone, a first polymer, (c) a water-soluble second polymer and (d) optionally, at least one pharmaceutical excipient; (ii) heating, mixing and kneading the resultant blend of step (i) via extruder to result in homogenous melt; (iii) forcing the resultant melt obtained in step (ii) through one or more orifices, nozzles, or moulds; (iv) cooling the extrudate of step (iii) by means of air to yield an amorphous Efavirenz ternary composition; and (v) optionally, grinding the solid dispersion obtained in step (iv).

A different embodiment of the present application relates to a method for preparing an amorphous Efavirenz ternary composition comprising the steps of: (i) preparing a homogenous blend of (a) Efavirenz, and (b) polyvinyl pyrrolidone, a first polymer; (ii) heating, mixing and kneading the resultant blend of step (i) via extruder to result in homogenous melt; (iii) forcing the resultant melt obtained in step (ii) through one or more orifices, nozzles, or moulds; (iv) cooling the extrudate of step (iii) by means of air; (v) optionally, grinding or milling the extrudate obtained in step (iv); and (vi) blending (a) cooled extrudate of step (iv) or milled material from step (v), and (b) a water-soluble second polymer to yield an amorphous Efavirenz ternary composition.

An additional embodiment of the present application relates to a method for preparing a solid dispersion composition comprising the steps of: (i) preparing a homogenous blend of (a) Efavirenz, and (b) polyvinyl pyrrolidone, a first polymer; (ii) heating, mixing and kneading the resultant blend of step (i) via extruder to result in homogenous melt; (iii) forcing the resultant melt obtained in step (ii) through one or more orifices, nozzles, or moulds; (iv) cooling the extrudate of step (iii) by means of air; (v) optionally, grinding or milling the extrudate of step (iv); and (vi) blending (a) cooled extrudate of step (iv) or milled material from step (v), (b) at least one pharmaceutical excipient and (c) a water-soluble second polymer to yield desired composition.

A critical embodiment of the present application relates to a stable and high loading ternary solid dispersion composition comprising: (a) about 50% wt. to about 90% wt. of amorphous Efavirenz; (b) about 10% wt. to about 50% wt. of polyvinyl pyrrolidone, a first polymer; (c) about 1% wt. to about 30% wt. of a water-soluble second polymer; and optionally about 0.1% wt. to about 50% wt. of at least one pharmaceutically acceptable excipient.

An extra embodiment of the present application relates to a method for preparing a ternary solid dispersion composition comprising the steps of: (i) preparing a homogenous aqueous and/or organic solution of (a) about 50% wt. to about 90% wt. of Efavirenz, (b) about 10% wt. to about 50% wt. of polyvinyl pyrrolidone, a first polymer, and (c) about 1% wt. to about 30% wt. of water-soluble second polymer; (d) optionally, about 0.1% wt. to about 50.0% wt. of at least one pharmaceutical excipients; and (ii) spray-drying the resultant homogenous solution of step (i) to yield a dry powder form of ternary solid dispersion composition.

Another embodiment of the present application relates to a method for preparing a ternary solid dispersion composition comprising the steps of: (i) preparing a homogenous blend of (a) about 50% wt. to about 90% wt. of Efavirenz, (b) about 10% wt. to about 50% wt. of polyvinyl pyrrolidone, a first polymer, (c) about 1% wt. to about 30% wt. of water-soluble second polymer and (d) optionally, about 0.1% wt. to about 50.0% wt. of pharmaceutical excipients; (ii) heating, mixing and kneading the resultant blend of step (i) via extruder to result in homogenous melt; (iii) forcing the resultant melt obtained in step (ii) through one or more orifices, nozzles, or moulds; (iv) cooling the extrudate of step (iii) by means of air to yield ternary solid dispersion; and (v) optionally, grinding the solid dispersion obtained in step (iv).

Another embodiment of the present application relates to a stable and high loading ternary composition comprising: (a) a solid dispersion composition comprising (i) about 50% wt. to about 90% wt. of amorphous Efavirenz; (ii) about 10% wt. to about 50% wt. of polyvinyl pyrrolidone, a first polymer; (b) about 1% wt. to about 30% wt. of a water-soluble second polymer blended with said solid dispersion of composition of (a); and (c) optionally about 0.1% wt. to about 50% wt. of at least one pharmaceutically acceptable excipient.

Yet another embodiment of the present application relates to a method for preparing a ternary composition comprising the steps of: (i) preparing a homogenous aqueous and/or organic solution of (a) about 50% wt. to about 90% wt. of Efavirenz, and (b) about 10% wt. to about 50% wt. of polyvinyl pyrrolidone, a first polymer; (ii) spray-drying the resultant homogenous solution of step (i) to yield a dry powder form of desired solid dispersion; (iii) blending the resultant solid dispersion of step (ii) with about 1% wt. to about 30% wt. of water-soluble second polymer to yield ternary composition; and wherein said organic solution is prepared from alcohols, ketones, alkyl acetates, chlorinated solvents, heterocyclic solvents, tetrahydrofuran and combination thereof.

Still another embodiment of the present application relates to a method for preparing a ternary composition comprising the steps of: (i) preparing a homogenous aqueous and/or organic solution of (a) about 50% wt. to about 90% wt. of Efavirenz, and (b) about 10% wt. to about 50% wt. of polyvinyl pyrrolidone, a first polymer; (ii) spray-drying the resultant homogenous solution of step (i) to yield a dry powder form of desired solid dispersion; (iii) blending the resultant solid dispersion of step (ii) with about 1% wt. to about 30% wt. of water-soluble second polymer to yield ternary composition; and about 0.1% wt. to about 50% wt. of at least one pharmaceutical excipients; and wherein said organic solution is prepared from alcohols, ketones, alkyl acetates, chlorinated solvents, heterocyclic solvents, tetrahydrofuran and combination thereof.

An additional embodiment of the present application relates to a method for preparing a ternary composition comprising the steps of: (i) preparing a homogenous blend of (a) about 50% wt. to about 90% wt. of Efavirenz, and (b) about 10% wt. to about 50% wt. of polyvinyl pyrrolidone, a first polymer; (ii) heating, mixing and kneading the resultant blend of step (i) via extruder to result in homogenous melt;

(iii) forcing the resultant melt obtained in step (ii) through one or more orifices, nozzles, or moulds; (iv) cooling the extrudate of step (iii) by means of air; (v) optionally, grinding or milling the extrudate of step (iv); and (vi) blending (a) cooled extrudate of step (iv) or milled material from step (v), (b) about 1% wt. to about 30% wt. of water-soluble second polymer, and (c) optionally, about 0.1% wt. to about 50% wt. of at least one pharmaceutical excipient.

Another embodiment of the present application relates to a method for preparing a tablet dosage form comprising the steps of: (i) preparing a solid dispersion comprising (a) about 50% wt. to about 90% wt. of Efavirenz, and (b) about 10% wt. to about 50% wt. of polyvinyl pyrrolidone, a first polymer; (ii) optionally, mill the resultant solid dispersion of step (i); (iii) optionally, blending resultant of step (i) or (ii) with about 0.1% wt. to 50% wt. of at least one pharmaceutical excipients; (iv) compressing the resultant of step (iii) into a tablet dosage form; and (v) coating the tablet of step (iv) with about 1% wt. to about 30% wt. of water-soluble second polymer.

According to one embodiment of the present application, the mixture of (a) Efavirenz, (b) PVP, a first polymer, and (c) at least one water-soluble second polymer is heated at a temperature wherein all the components of the mixture are melted, or a temperature wherein some components are melted. Hot-melt extrusion wherein the melting refers to a transition of components into a liquid or rubbery stage in which it allows one or more component to get embedded homogenously in the other component. The preparation of hot-melt extrusion comprises (a) Efavirenz, a desired API, (b) PVP, a first polymer, and (c) at least one water-soluble second polymer is mixed together and soft mass is produced. Alternatively, the mixing of Efavirenz, PVP, and a water-soluble second polymer can happen before, during or after the formation of the soft mass. For example, the required ingredients to produce the soft mass may be mixed initially and then extruded, or may be simultaneously mixed and melt extruded. Finally, the hot-melt is homogenized so as to disperse or embed the Efavirenz into other ingredients or components.

The process of hot-melt extrusion is carried out by using conventional extruders that are known in the prior-arts for a person skilled in the art. The suitable extruders include, but not limited to, single screw extruders, intermeshing screw extruders or else multi-screw extruders, preferably twin screw extruders, which can be co-rotating or counter-rotating and, optionally, be equipped with kneading, mixing and/or conveying elements. The working temperature for preparing hot-melt extrusion typically depends on the API and polymer properties as well as extruder type and screw configuration.

The extrudate obtained from extrusion may be in the form of beads, granulates, tube, strand, or cylinder and this can be further processed into any suitable shape. The term "extrudate" herein refers to glass solutions and amorphous and crystalline solid dispersions, and of Efavirenz, PVP, a water-soluble second polymer and optionally one or more pharmaceutically acceptable excipients.

According to one embodiment of the present application, the alternative methods for preparing solid dispersion would include, but are not limited to, fusion/melt technology, hot-melt coating, prilling, melt-congealing, melt-granulation, spray-congealing, solvent-evaporation, spray-drying, co-precipitation, co-melting, supercritical fluid method, and electrostatic spinning method.

According to one particularly preferred embodiment of this application, (a) Efavirenz, (b) PVP, a first polymer and (c) methyl cellulose (MC), or hydroxypropyl methyl cellulose (HPMC) or hydroxypropyl methyl cellulose acetate succinate (HPMCAS), or hydroxypropyl cellulose (HPC) or hydroxyethyl cellulose (HEC), or hydroxymethyl ethyl cellulose (HMEC) or hydroxypropyl methyl cellulose phthalate (HPMCP), a water-soluble second polymer are melt extruded and milled by the process as described herein, to produce a powder blend of (a) Efavirenz, (b) PVP, (c) MC or HPMC or HPMCAS or HPC or HEC or HMEC or HPMCP and (d) optionally, one or more pharmaceutically acceptable excipients which may comprise processing aid suitable bulking agents, plasticizer, surfactants, plasticizers, disintegrants, lubricants, glidants, carriers, anti-adherents, inert fillers, wetting agents, pH modifiers, binders, solubility modifiers, and/or recrystallization inhibitors.

According to another particularly preferred embodiment of this application, (a) Efavirenz, (b) PVP, a first polymer and (c) MC or HPMC or HPMCAS or HPC or HEC or HMEC or HPMCP, a water-soluble second polymer are spray-dried by the process as described herein, to produce a spray-dried powder blend of (a) Efavirenz, (b) PVP, (c) MC or HPMC or HPMCAS or HPC or HEC or HMEC or HPMCP and (d) optionally, one or more pharmaceutically acceptable excipients which may comprise processing aid suitable bulking agents, plasticizer, surfactants, plasticizers, disintegrants, lubricants, glidants, carriers, anti-adherents, inert fillers, wetting agents, pH modifiers, binders, solubility modifiers, and/or recrystallization inhibitors.

The high loading amorphous Efavirenz ternary composition of the present application can be advantageously formulated with or without pharmaceutically acceptable additives. The preferred dosage formulation of the present application would include, but not limited to, powder, granules, fine granules, tablets, rings, capsules, pellets, suppositories, ointments, plasters, cataplasms, aerosols, powders and the like.

Further, the invention of present application is illustrated in-detail by way of the below given examples. The examples are given herein for illustration of the invention and are not intended to be limiting thereof.

Example 1

Process for Preparing Ternary Solid Dispersion Compositions (Table 1; 5211-101 to 5211-215)

Solution Preparation: The respective amounts of Efavirenz and polymers were dissolved in a 2:1 (w/w) mixture of Acetone: Methanol solution at a total 3% solid loading. Dissolution of all components was visually confirmed before spray drying.

Spray Drying: Spray drying was performed on a GEA-Niro SD Micro spray dryer. All dispersions (refer Table 1; 5211-101 to 5211-215) were spray dried targeting an inlet gas temperature of 85° C., 25 kg/hr process gas flow, 0.5 bar atomization gas pressure, 1.5 kg/hr atomizing gas flow, and an adjustable liquid feed rate targeting an outlet gas temperature of 55° C. The feed solution was held at ambient conditions.

GEA-Niro SD MICRO™ Spray Dryer: The unit possesses a chamber with an inside diameter of 211 mm (8.3 inches) and a 350 mm (13.75 inches) cylindrical height (straighter side) with a 60° angle conical bottom. The flow pattern is configured in a co-current arrangement, with the drying gas and feed materials entering at the top of the dryer. Approximately 25 kg/hr electrically heated Nitrogen was utilized as drying gas and enters the drying chamber through an air dispenser concentric with the nozzle. Product is collected in a cyclone collector. A small bag house filter collects all of the fines before gas leaves the system, this collection was not included in the sampling. The system is run under a slight positive pressure to assure against the incursion of air. The feed material was atomized using a 0.5 mm two-fluid Niro nozzle for all runs. Collection of the product is at the cyclone. A variable speed peristaltic pump, Master Flex, equipped with Tygon Chemical tubing, was used to deliver the feed material.

Secondary Drying: Spray dried dispersions were vacuum oven dried for 65 hours at 35 to 45° C. to remove residual solvent present if any.

Blending: Mixtures of respective spray dried binary solid dispersions (refer Table 1, 5211-103; 5211-106; 5211-110; 5211-114; 5211-208 to 5211-215) and the appropriate polymers were lightly triturated in a mortar and pestle to effectively blend the materials to result desired high loading ternary solid dispersion composition.

Example 2

Evaluation of Physical Stability of Binary and Co-Processed Ternary Solid Dispersions Through XPRD X-ray Powder Diffraction (XRPD) Method: It was performed for all the binary or co-processed ternary solid dispersion compositions listed in Table 1 (5211-101 to 5211-115) on a Bruker D8 Focus, using a copper tube element and a PSD: LynxEye detector. The following data acquisition parameters were used: Volts: 40 kV, Amps: 40 mA, Scan Range: 4.0000°-39.9960° 2θ, Number of Steps: 1685, Time/step: 0.3 s, Collection Time: 549 s, Rotation Speed: 15 rpm, Mode: Continuous.

Figure 2:
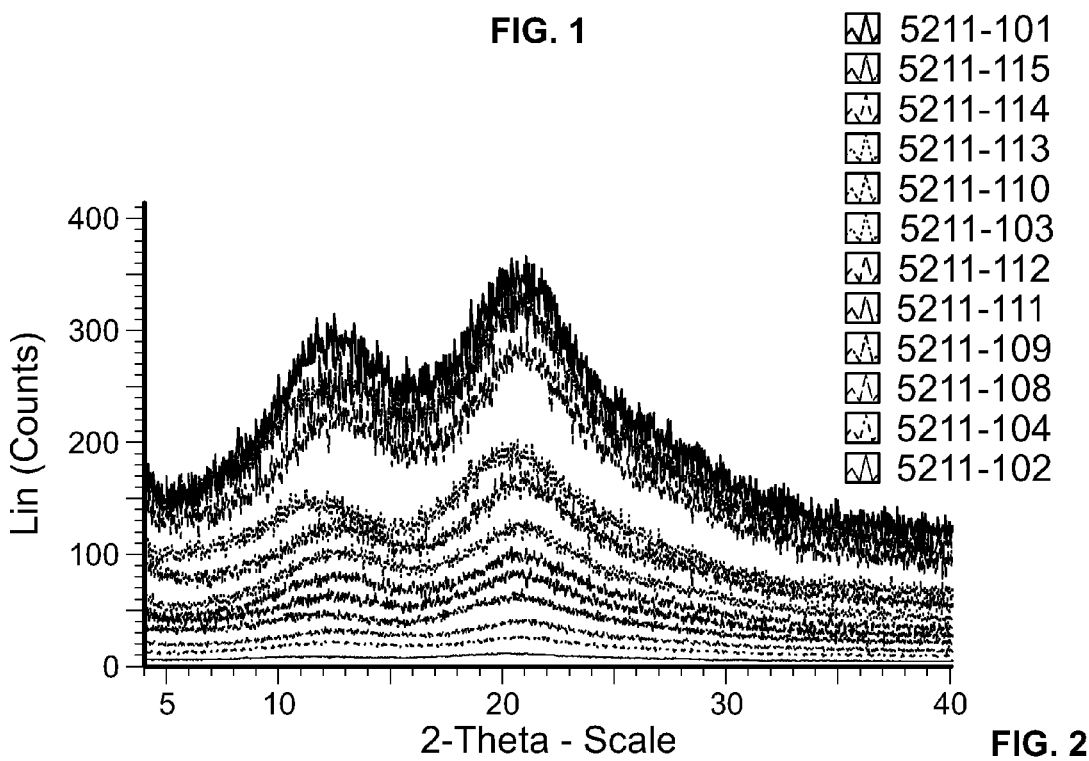
FIG. 2 is an illustration of XRPD patterns of binary and co-processed ternary spray-dried solid dispersions (5211-101 to 104; and 5211-108 to 115) after 1-month storage at 25° C., 60% RH.

Dried Compositions Analysis: The XRPD analysis results demonstrated that all the binary or co-processed ternary spray-dried solid dispersions (FIG. 1) are amorphous after spray-drying and secondary (vacuum oven) drying. The XRPD analysis of binary or co-processed ternary spray-dried solid dispersions (FIG. 2) after 1 month storage at 25° C. and 60% relative humidity (RH) were found to be amorphous.

TABLE 1

Types of ternary solid dispersion formulations and their ratio

| Sample | Ratio of Efavirenz to Polymers | |
|---|---|---|
| No. | Spray-Dried | Blended |
| 5211-101 | Efavirenz:PVP (5:5) | — |
| 5211-102 | Efavirenz:HPMC (5:5) | — |
| 5211-103 | Efavirenz:PVP (5:4) | HPMC (1) |
| 5211-104 | Efavirenz:PVP:HPMC (5:4:1) | — |
| 5211-105 | Efavirenz:Copovidone(5:5) | — |
| 5211-108 | Efavirenz:PVP (7:3) | — |
| 5211-109 | Efavirenz:HPMC (7:3) | — |
| 5211-110 | Efavirenz:PVP (7:2) | HPMC (1) |
| 5211-111 | Efavirenz:PVP:HPMC (7:2:1) | — |
| 5211-112 | Efavirenz:PVP (6:4) | — |
| 5211-113 | Efavirenz:HPMC (6:4) | — |
| 5211-114 | Efavirenz:PVP (6:3) | HPMC (1) |
| 5211-115 | Efavirenz:PVP:HPMC (6:3:1) | — |
| 5211-202 | Efavirenz:HPMCAS (7:3) | — |
| 5211-203 | Efavirenz:HPMCP (7:3) | — |
| 5211-204 | Efavirenz:MA Copolymer L100 (7:3) | — |
| 5211-208 | Efavirenz:PVP (7:3) | HPMC (5%) |
| 5211-209 | Efavirenz:PVP (7:3) | HPMC (10%) |
| 5211-210 | Efavirenz:PVP (7:3) | HPMC (15%) |
| 5211-214 | Efavirenz:PVP (7:3) | HPC (10%) |
| 5211-215 | Efavirenz:PVP (7:3) | MC (10%) |

Figure 3:
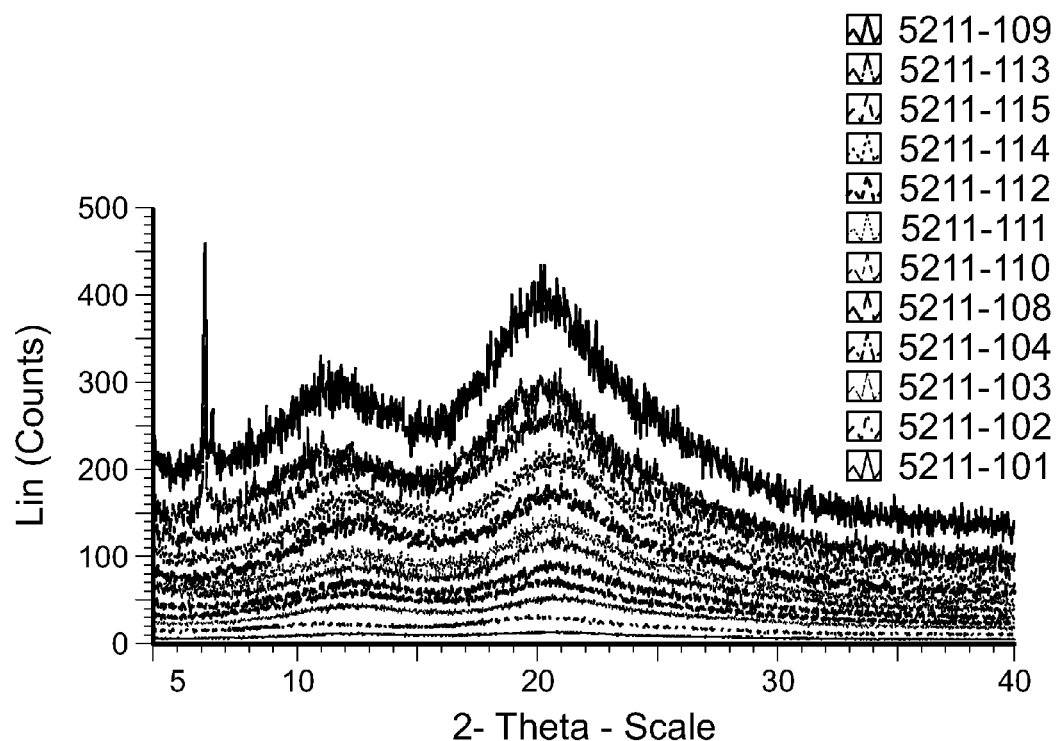
FIG. 3 is an illustration of XRPD patterns of binary and co-processed ternary spray-dried solid dispersions (5211-101 to 104; and 5211-108 to 115) after 1-month storage at 40° C., 75% RH.
Figure 4:
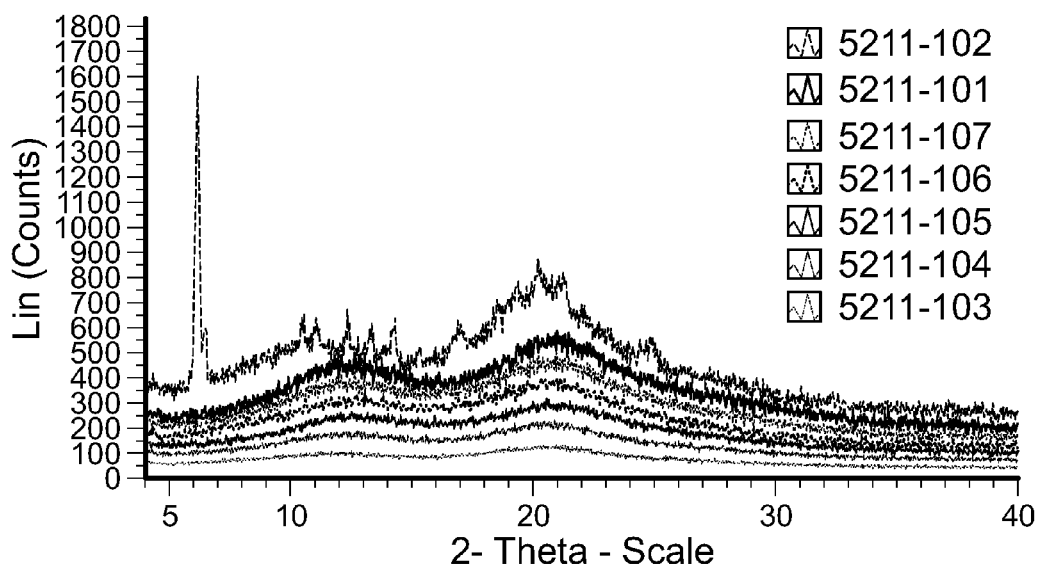
FIG. 4 is an illustration of XRPD patterns of binary and co-processed ternary spray-dried solid dispersions (5211-101 to 107) after 2-month storage at 40° C., 75% RH.
Figure 5A:
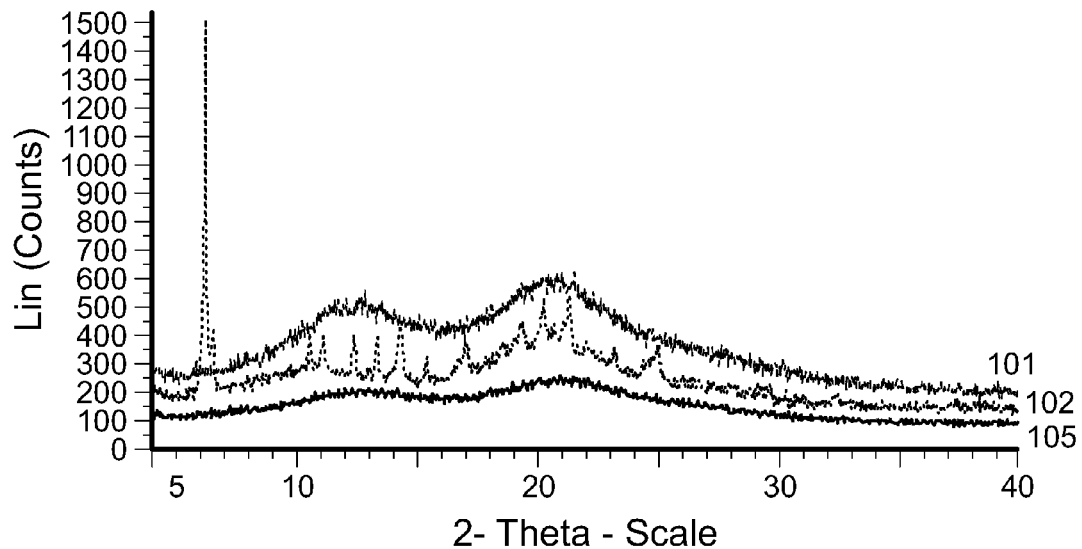
FIG. 5a is an illustration of XRPD patterns of binary spray-dried solid dispersions (5211-101, 102 and 105) after 3-month storage at 40° C., 75% RH.
Figure 5B:
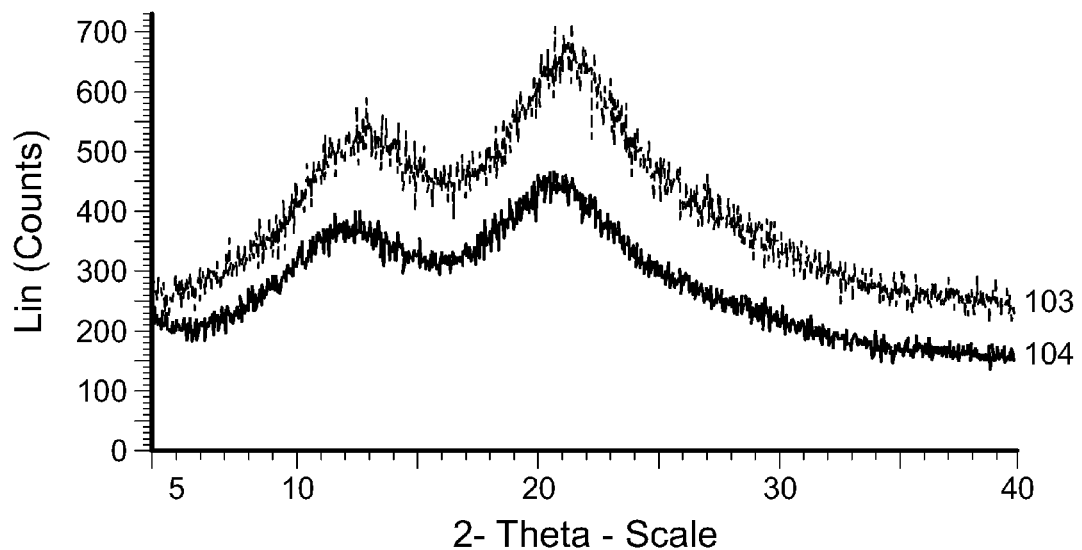
FIG. 5b is an illustration of XRPD patterns of binary and co-processed ternary spray-dried solid dispersions (5211-103 and 104) after 3-month storage at 40° C., 75% RH.
Figure 5C:
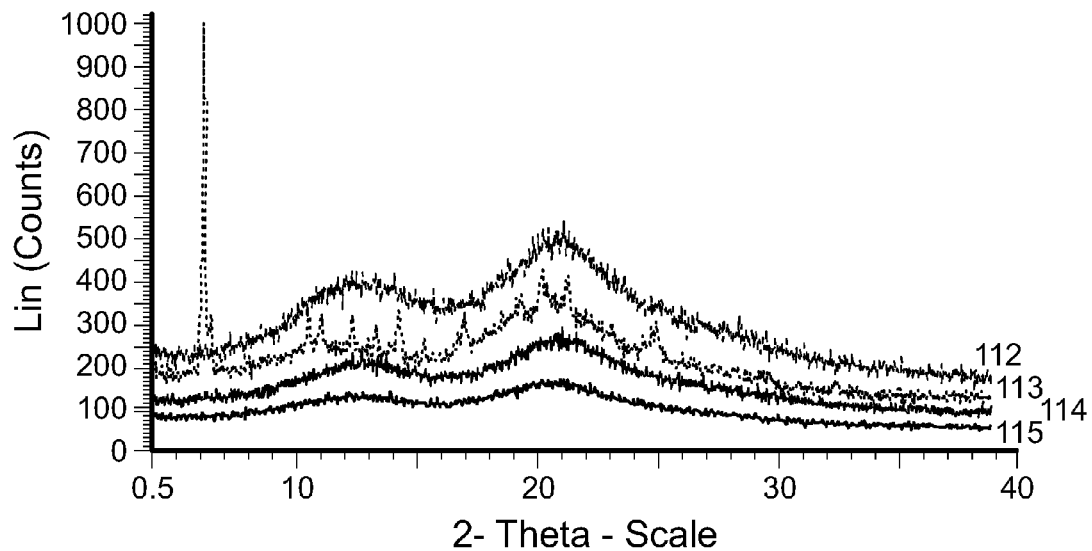
FIG. 5c is an illustration of XRPD patterns of binary and co-processed ternary spray-dried solid dispersions (5211-112, 113, 114 and 115) after 3-month storage at 40° C., 75% RH.
Figure 5D:
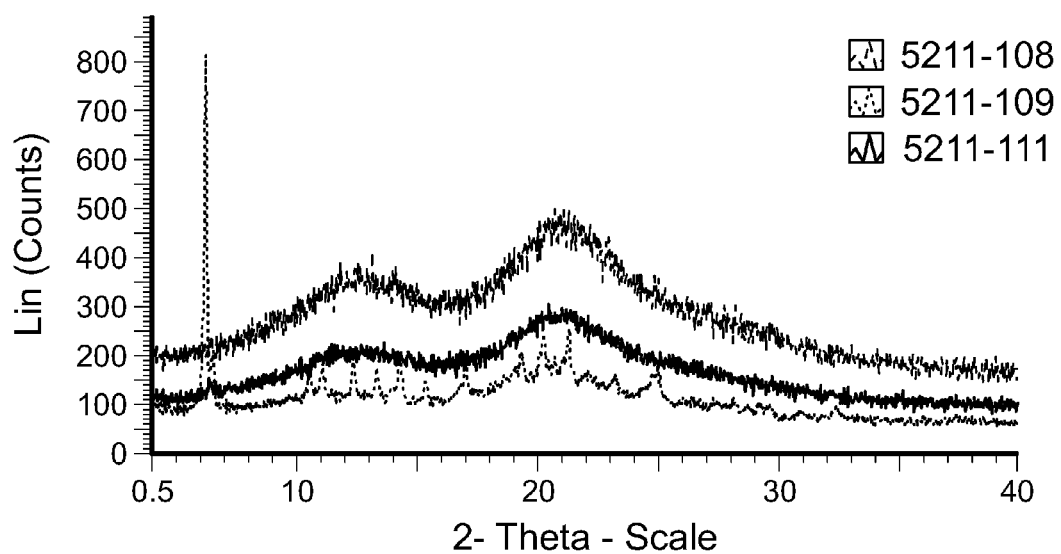
FIG. 5d is an illustration of XRPD patterns of binary and co-processed ternary spray-dried solid dispersions (5211-108, 109, and 111) after 3-month storage at 40° C., 75% RH.
Figure 6:
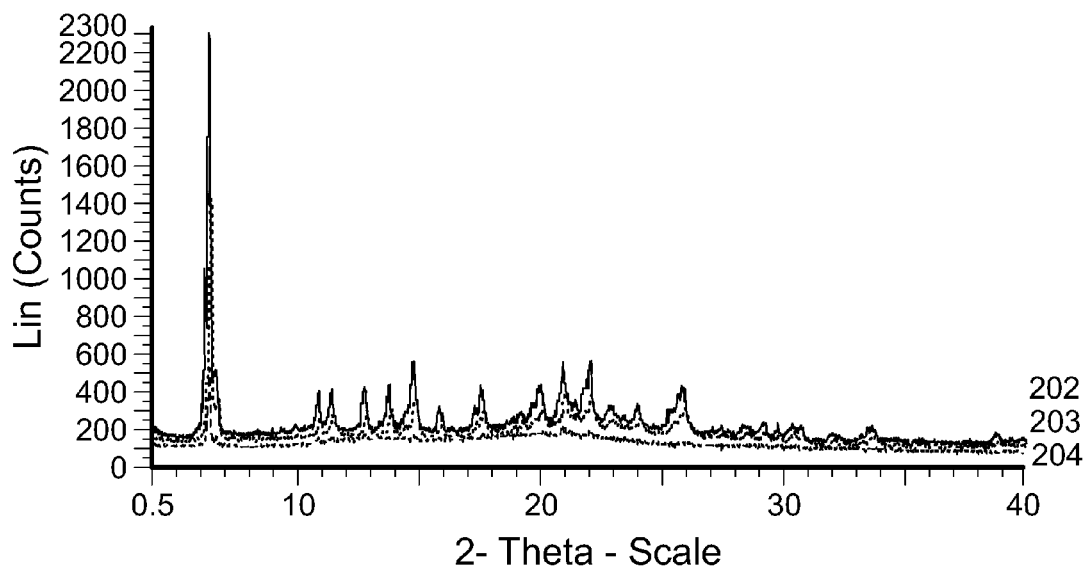
FIG. 6 is an illustration of XRPD patterns of binary spray-dried solid dispersions (5211-202, 203 and 204) after 3-month storage at 40° C., 75% RH.

Physical Stability Study: The accelerated stability study was performed by placing the solid dispersion compositions (5211-101- to 5211-115) in a stability chamber at 40° C., 75% RH for 1 month and re-analyzed by XRPD, and all the co-blends/co-processed compositions were amorphous (FIG. 3) except Efavirenz: HPMC, 7:3 (5211-109) and Efavirenz: HPMC, 6:4 (5211-113). Under the same stability conditions, the compositions were placed in stability chamber for 2 months and re-analysed by XRPD, the results demonstrated that the binary or co-processed ternary spray-dried solid dispersions (FIG. 4) were still amorphous even after 2 months accelerated stress storage except for Efavirenz: HPMC, 5:5 (5211-102). Further, the three-month stability study of the same group of spray dried solid dispersions (FIG. 5a-d) under the same accelerated stress revealed to be amorphous in nature except for Efavirenz: HPMC, 5:5 (5211-102). The three-month physical stability study of solid dispersion compositions comprising (1) Efavirenz and (2) HPMCAS or HPMCP or Methacrylic Acid (MA) copolymer recrystallized after 3 month of storage in an accelerated stability chamber at 40° C., 75% RH as indicated in FIG. 6.

When served as primary solid dispersion carrier, PVP outperformed other polymers and was able to maintain stability at high drug load (>50 to 70 w/w %) under accelerated conditions for at least 3 months.

Example 3

Evaluation of Kinetic Solubility of Solid Dispersions (5211-101 to 111; and 5211-202 to 210)

Kinetic Solubility in Fasted State Simulated Intestinal Fluid (FaSSIF):

The kinetic solubility study was performed using the following method: excess powder of solid dispersion samples or co-blended samples were added in a vial containing 30 mL of fasted state simulated intestinal fluid (FaSSIF), then shaken under constant oscillatory motion at 37° C. Aliquots are pulled at 10, 20, 30, 45, 60, 90, 120, 180, and 200 minutes, centrifuged and diluted with organic solvent before being assayed for Efavirenz concentration using a validated HPLC method.

Figure 7A:
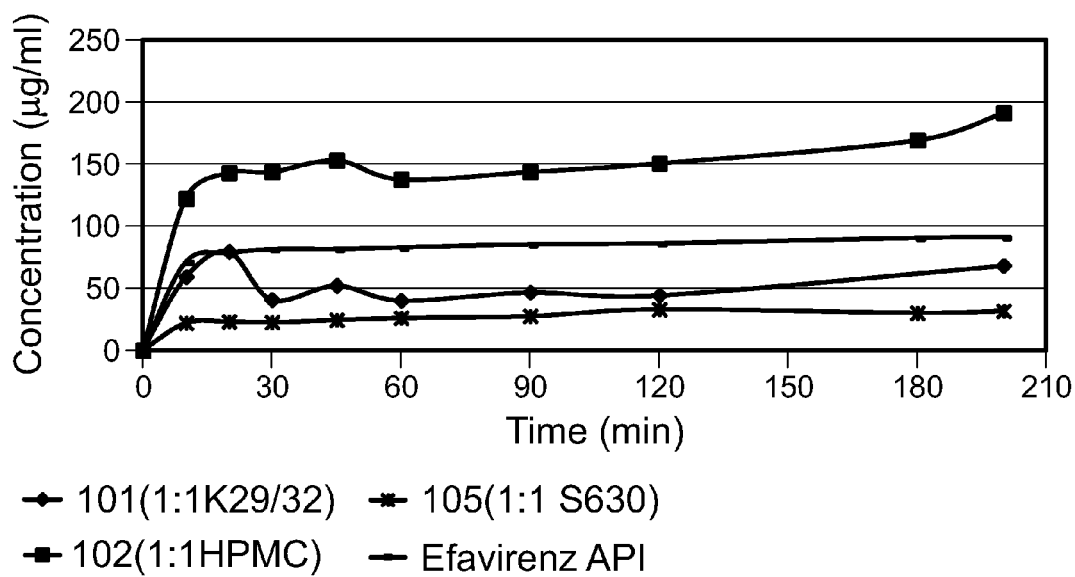
FIG. 7a is an illustration of kinetic solubility of Efavirenz solid dispersions (5211-101, 102, and 105) with PVP or copovidone or HPMC (Efavirenz: polymer ratio: 1:1).
Figure 7B:
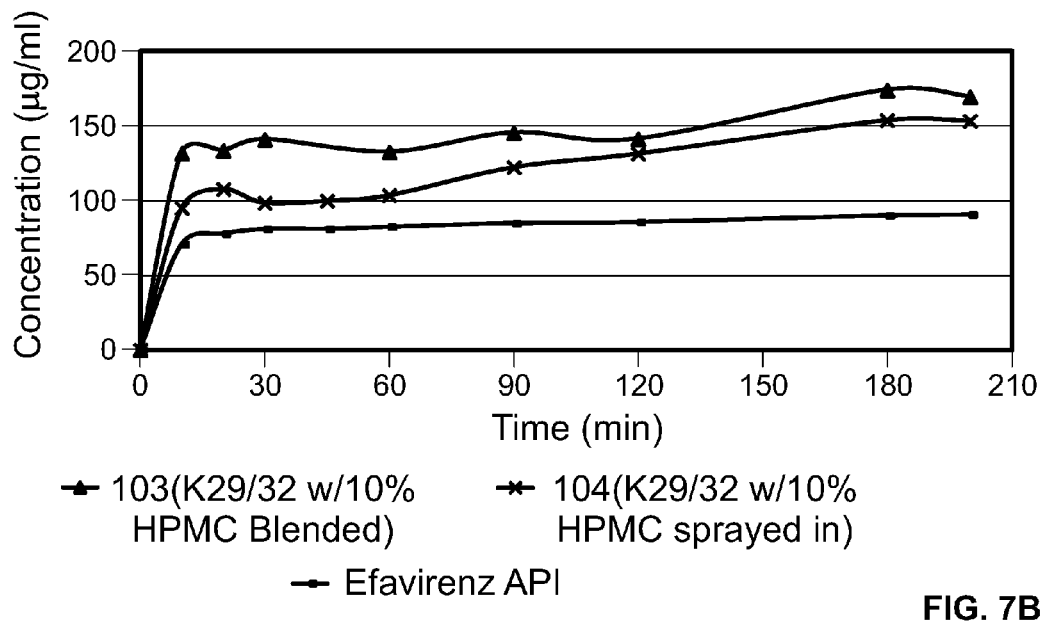
FIG. 7b is an illustration of kinetic solubility of Efavirenz: PVP 5:4 solid dispersion (5211-103 and 104) and its co-spray dried or co-blended mixture with 10% HPMC.

From the kinetic solubility study (FIG. 7a-b), it was observed that the Efavirenz: HPMC 5:5 (Sample No. 102) composition demonstrated excellent kinetic solubility (FIG. 7a), but the formulation is physically unstable and crystallized at accelerated conditions after 3 months (FIG. 5a). The binary solid dispersion of Efavirenz and PVP (5:5, Sample No. 101) showed delayed dissolution in comparison with the crystalline Efavirenz. However, as indicated in FIG. 7b, when Efavirenz:PVP (5:4) solid dispersion is blended with 10% HPMC (Sample No. 103), it significantly out-performed Efavirenz: PVP solid dispersion (5:5, Sample No. 101) and co-spray-dried Efavirenz: PVP:HPMC (5:4:1, Sample No. 104) solid dispersion. Similar result was observed when HPMC was co-blended or co-processed with Efavirenz: copovidone solid dispersions. The above results demonstrated that by adding a suitable recrystallization inhibitor such as HPMC, the dissolution performance of the Efavirenz: PVP or copovidone solid dispersions can be enhanced significantly Kinetic Solubility in Simulated Gastric Fluid (SGF) and Fasted State Simulated Intestinal Fluid (FaSSIF):

To assess the kinetic solubility of spray dried dispersion, excess powder of solid dispersion samples were added in a vial containing Simulated Gastric Fluid (SGF), then shaken under constant oscillatory motion at 37° C. Aliquots are pulled at 10, 20, 30, 45, 60, 90, and 120 minutes. After 120 minutes, a concentrated Fasted State Simulated Intestinal Fluid (cFaSSIF) is added to the sample containing SGF solution, and then shaken under constant oscillatory motion at 37° C. Aliquots are pulled at 10, 20, 30, 45, 60, 90, 120, 180, and 200 minutes, centrifuged and diluted with organic solvent before being assayed for Efavirenz concentration using a validated HPLC method.

Figure 8A:
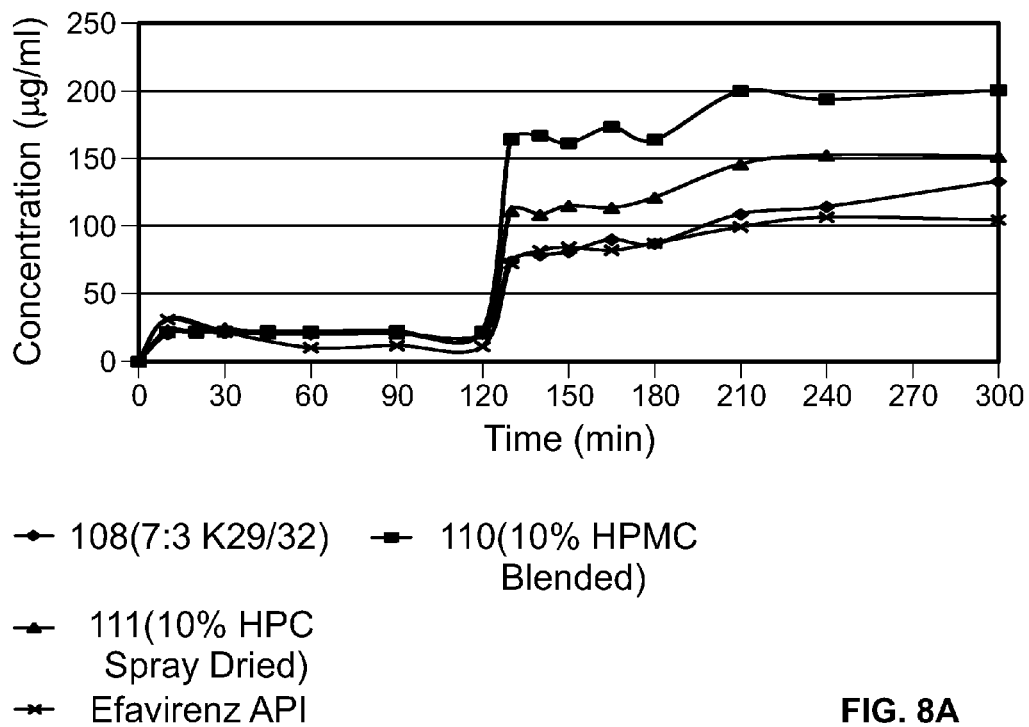
FIG. 8a is an illustration of kinetic solubility of Efavirenz: PVP 7:3 solid dispersions and its co-spray dried and co-blended mixtures with 10% HPMC (5211-108, 110 and 111).
Figure 8B:
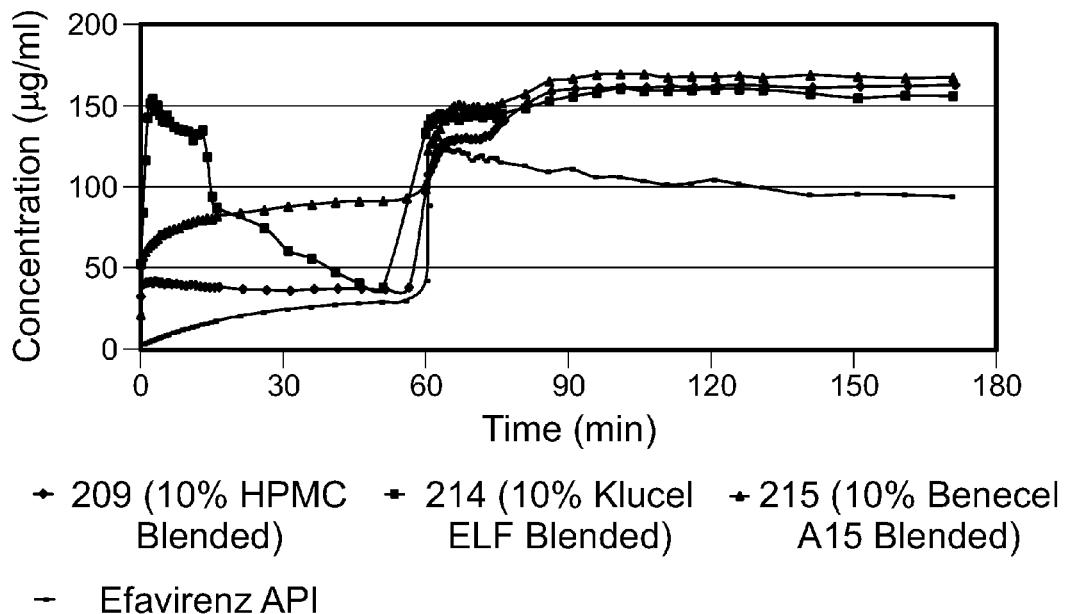
FIG. 8b is an illustration of kinetic solubility of co-blended mixtures of Efavirenz: Copovidone 7:3 solid dispersions with 10% HPMC or HPC or MC (5211-209, 214 and 215).
Figure 8C:
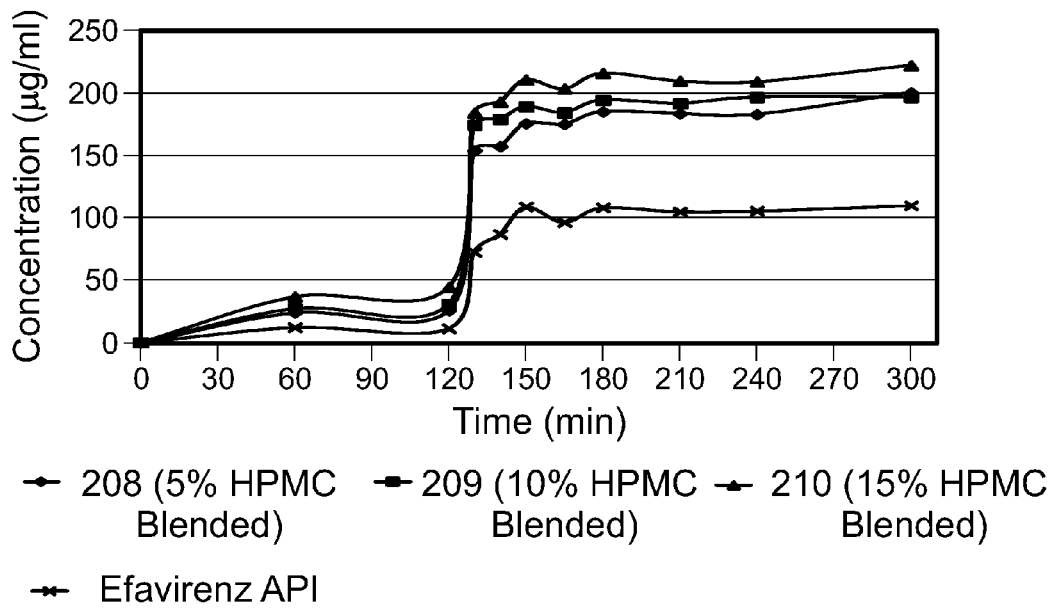
FIG. 8c is an illustration of kinetic solubility of co-blended mixtures of Efavirenz: PVP7:3 solid dispersions with different amount of HPMC (5211-208, 209 and 210).

The kinetic solubility study (FIG. 8a) of binary or ternary solid dispersions or solid dispersion blend with HPMC exhibited that at 70% drug load, and HPMC was again an effective precipitation inhibitor, it was able to significantly improve the dissolution performance of Efavirenz: PVP solid dispersion. Also, the co-blended mixture is more effective than the co-spray dried mixture in enhancing the dissolution. Further, the kinetic solubility of Efavirenz: Copovidone 7:3 solid dispersions were enhanced when mixed with 10% HPC or MC (FIG. 8b). The dissolution enhancing effect of both polymers was similar with that of HPMC. As demonstrated in FIG. 8c, by increasing the percentage of HPMC which is blended with Efavirenz: Plasdone solid dispersion, the dissolution performance can be modified, and the higher use level of precipitation inhibitor HPMC contributed to better dissolution performance.

Example 4

Preparation and Characterization of Ternary Solid Dispersion Composition Using PVP K29/32 as Primary Polymer Efavirenz, PVP K29/32 and Vitamin E TPGS blends (6/3/1 w/w/w, 1000 g) were extruded using a Lestritz ZSE 18HP co-rotating twin-screw extruder. The extruder comprises eight heating zones. The heating zones were maintained at a temperature between 50° C. and 175° C., with a gradual increase of temperature from zone 1 to zone 8. The sample was extruded at approximately 100 rpm.

The extrudate obtained was confirmed by XRPD and DSC as amorphous, and the solid dispersion maintains its amorphous nature for longer than 3 months under ambient storage condition. The dissolution of Efavirenz from the solid dispersion has significantly improved in comparison with the crystalline API.

Example 5

Preparation and Characterization of Ternary Solid Dispersion Composition Using PVP K-12 as Primary Polymer Efavirenz, PVP K-12 and HPMC blends (6/3/1 w/w/w, 1000 g) were extruded using a Lestritz ZSE 18HP co-rotating twin-screw extruder. The extruder comprises eight heating zones. The heating zones were maintained at a temperature between 50° C. and 170° C., with a gradual increase of temperature from zone 1 to zone 8. The sample was extruded at approximately 50 rpm.

The extrudate obtained was confirmed by XRPD and DSC as amorphous, and the solid dispersion maintains its amorphous nature for longer than 3 months under ambient storage condition. The dissolution of Efavirenz from the solid dispersion has significantly improved in comparison with the crystalline API.

Example 6

Preparation and Characterization of Binary Solid Dispersion Composition Using PVP K-12 as Primary Polymer Efavirenz and PVP K-12 blends (6/3 w/w, 1000 g) were extruded using a Lestritz ZSE 18HP co-rotating twin-screw extruder. The extruder comprises eight heating zones. The heating zones were maintained at a temperature between 50° C. and 160° C., with a gradual increase of temperature from zone 1 to zone 8. The sample was extruded at approximately 150 rpm.

The extrudate obtained was confirmed by XRPD and DSC as amorphous, and the solid dispersion maintains its amorphous nature for longer than 3 months under ambient storage condition. After blending the solid dispersion with 10% HPMC, the dissolution of the powder mixture has significantly improved and the supersaturation of Efavirenz is further extended in comparison with the crystalline API.

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope and spirit of this invention.

What is claimed is:

1. A stable and high loading ternary solid dispersion composition comprising:
   a. about 50% wt. to about 90% wt. of amorphous Efavirenz;
   b. about 10% wt. to about 50% wt. of polyvinyl pyrrolidone, a first polymer;
   c. about 1% wt. to about 30% wt. of a water-soluble second polymer; and
   d. optionally about 0.1% wt. to about 50% wt. of at least one pharmaceutically acceptable excipient.

2. The ternary solid dispersion composition according to claim 1, wherein the ratio of Efavirenz (a) to first polymer (b) to water-soluble second polymer (c) is about 1.0:0.5-1.0:0.05-0.5.

3. The ternary solid dispersion composition according to claim 1, wherein the average molecular weight of polyvinyl pyrrolidone is in the range of from about 4,000 to about 130,000,00.

4. The ternary solid dispersion composition according to claim 1, wherein the molecular weight of polyvinyl pyrrolidone is in the range of from about 25,000 to about 35,000.

5. The ternary solid dispersion composition according to claim 1, wherein said water-soluble second polymer is selected from the group consisting of cellulose esters, cellulose ethers, polyacrylates, polymethacrylates, acrylates copolymers, homo and co polymers of acrylic acids, homo and co polymers of methacrylic acids, copolyacrylamides, polyvinyl alcohols, polyvinylpyrrolidone, polyvinylpyrrolidone/vinyl acetate copolymer, carboxyvinyl polymers, oligosaccharides, and/or polysaccharides.

6. The ternary solid dispersion composition according to claim 1, wherein said water-soluble second polymer is selected from the group consisting of hydroxypropyl methyl cellulose succinate, cellulose acetate succinate, methyl cellulose acetate succinate, ethyl cellulose acetate succinate, hydroxypropyl cellulose acetate succinate, hydroxypropyl methyl cellulose acetate succinate (HPMCAS), hydroxypropyl cellulose acetate phthalate succinate, cellulose propionate succinate, hydroxypropyl cellulose butyrate succinate, hydroxypropyl methyl cellulose phthalate (HPMCP), cellulose acetate phthalate, methyl cellulose acetate phthalate, ethyl cellulose acetate phthalate, hydroxypropyl cellulose acetate phthalate, hydroxypropyl methyl cellulose acetate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, ethyl picolinic acid cellulose acetate, carboxy methyl cellulose, carboxy ethyl cellulose, ethyl carboxy methyl cellulose, hydroxypropyl methyl cellulose acetate, hydroxypropyl methyl cellulose (HPMC), hydroxypropyl cellulose, methyl cellulose, hydroxyethyl methyl cellulose, hydroxyethyl cellulose acetate, and hydroxyethyl ethyl cellulose, copolymers of methacrylates, copolymers of acrylates, poly(methacylic acid-co-methyl methacrylate), alone or in combination.

7. The ternary solid dispersion composition according to claim 1, wherein the composition is storage-stable, transit-stable and/or able to increase dissolution rate and/or maintain supersaturation of Efavirenz (a) during dissolution.

8. The ternary solid dispersion composition according to claim 1, wherein said pharmaceutically acceptable excipients is selected from the group consisting of plasticizers, disintegrants, surfactants, lubricants, glidants, carriers, anti-adherents, fillers, wetting agents, pH modifiers, binders, solubility modifiers, recrystallization inhibitors, coating agent and/or diluents.

9. The ternary solid dispersion composition according to claim 8, wherein said plasticizer is selected from the group consisting of Triethyl Citrate, Glycerol Monostearate, Dibutyl Sebacate, Diethyl Phthalate, Polyethylene Glycol, Triacetin, Vitamin E-TPGS, Tween 80, Sodium Lauryl Sulfate, Sodium Docusate, Poloxamer F-68, Poloxamer F-127, Hydroxypropyl cellulose, polyvinyl caprolactam-polyvinyl acetate-polyethylene glycol graft copolymer, alone or in combination.

10. The ternary solid dispersion composition according to claim 1, wherein the pharmaceutical excipient is plasticizer present in an amount of from about 0.1% wt. to about 10.0% wt. of the total composition.

11. The ternary solid dispersion composition according to claim 1, wherein said solid dispersion is formulated into tablets, films, capsules, pellets, granules, fine granules or a powder.

12. The ternary solid dispersion composition according to claim 1, wherein the composition is prepared by spray-drying, hot-melt extrusion, solvent-evaporation, melt-granulation, melt-congealing, spray-congealing, blending, co-milling, spray coating, fluid bed granulation, layering or coating.

* * * * *